United States Patent [19]

Kane et al.

[11] Patent Number: 4,981,863

[45] Date of Patent: Jan. 1, 1991

[54] 3-ARYL-5-ALKYLTHIO-4H-1,2,4-TRIAZOLES

[75] Inventors: John M. Kane, Cincinnati; Francis P. Miller, Loveland, both of Ohio

[73] Assignee: Merrell Dow Pharmaceuticals, Cincinnati, Ohio

[21] Appl. No.: 463,082

[22] Filed: Jan. 10, 1990

Related U.S. Application Data

[60] Division of Ser. No. 126,191, Dec. 4, 1987, Pat. No. 4,900,743, which is a continuation-in-part of Ser. No. 7,063, Jan. 27, 1987, abandoned.

[51] Int. Cl.$^5$ .................... C07D 249/12; A61K 31/41
[52] U.S. Cl. .................... 514/384; 548/263.2; 548/264.2
[58] Field of Search .................... 514/384; 548/263.2, 548/264.2

[56] References Cited

U.S. PATENT DOCUMENTS

| | | | |
|---|---|---|---|
| 3,037,916 | 6/1962 | Goodman | 195/80 |
| 3,308,131 | 3/1967 | McKusick | 598/266.8 |
| 4,120,864 | 10/1978 | Seidel et al. | 548/263.2 |
| 4,414,221 | 11/1983 | Parsons et al. | 424/269 |

FOREIGN PATENT DOCUMENTS

| | | | |
|---|---|---|---|
| 155486 | 9/1985 | European Pat. Off. | 548/263.2 |
| 42-3096 | 2/1967 | Japan . | |
| 50-63119 | of 1975 | Japan . | |
| 845715 | 8/1960 | United Kingdom . | |

OTHER PUBLICATIONS

G. Mazzone and F. Bonina, *Il Farmaco, Ed. Sci.*, 36(12), 1004–1018 (1981).
K. C. Joshi and D. S. Mehta, *J. Indian Chem. Soc.*, 51(6), 613–15 (1974).
F. Russo and M. Ghelardoni, *Boll. Chim. Farm.*, 108, 128–39 (1969).
E. Hoggarth, *J. Chem. Soc.*, 1949, 1160–63.
M. Y. Mhasalkar et al., *J. Med. Chem.*, 14(3), 260–2.
B. N. Goswami et al., *J. Heterocyclic Chem.*, 21, 1225–9 (1984).

*Primary Examiner*—Glennon H. Hollrah
*Assistant Examiner*—Patricia L. Morris
*Attorney, Agent, or Firm*—Edlyn S. Simmons

[57] ABSTRACT

This invention relates to derivatives of 3-aryl-5-alkylthio-4H-1,2,4-triazoles, to their pharmacological properties and to their use as muscle relaxants, spasmolytics, anticonvulsants and anxiolytics.

8 Claims, No Drawings

3-ARYL-5-ALKYLTHIO-4H-1,2,4-TRIAZOLES

CROSS REFERENCE TO RELATED APPLICATION

This is a division of application Ser. No. 126,191, filed Dec. 4, 1987, now U.S. Pat. No. 4,900,743, which is a continuation-in-part of application Ser. No. 7,063, filed Jan. 27, 1987 now abandoned.

SUMMARY OF THE INVENTION

This invention relates to derivatives of 3-aryl-5-alkylthio-4H-1,2,4-triazoles, to the intermediates and processes for their preparation, and to their pharmacological properties and to their use as muscle relaxants, spasmolytics, anticonvulsants and anxiolytics.

More specifically this invention relates to the use of compounds of formula I and their pharmaceutically acceptable salts as muscle relaxants, spasmolytics, anticonvulsants and anxiolytics;

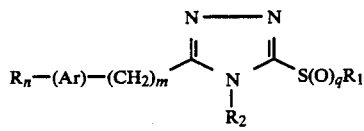

wherein

Ar is phenyl, naphthyl, or a monocyclic heteroaryl moiety selected from thienyl, pyridyl, pyrrolyl, and N-($C_{1-6}$ lower alkyl)pyrrolyl;

$R_1$ is $C_{1-6}$ lower alkyl;

$R_2$ is hydrogen or $C_{1-6}$ lower alkyl;

R is $C_{1-6}$ lower alkyl, $C_{1-6}$ alkoxy, hydroxy, halogeno, or trifluoromethyl and n is zero, 1 or 2, or $R_n$-(Ar) is methylenedioxyphenyl; and each of m and q is zero, 1 or 2.

Another aspect of this invention relates to novel 5-aryl-3-alkylsulfinyl-4H-1,2,4-triazoles of formula II,

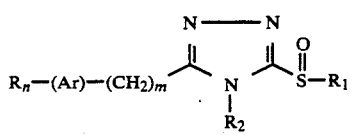

wherein Ar, $R_1$, $R_2$, R, m and n have the meanings defined above.

Another aspect of this invention relates to novel 5-aryl-3-alkylsulfonyl-4H-1,2,4-triazoles of formula III,

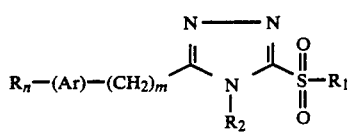

wherein Ar, $R_1$, $R_2$, R, m and n have the meanings defined above, with the provisos that (1) $R_n$-Ar-(CH$_2$)m is other than 2-ethoxyphenyl; that (2) when $R_n$-(Ar)-(CH$_2$)$_m$ is phenyl and $R_1$ is methyl, $R_2$ is $C_{1-6}$ lower alkyl; and that (3) when $R_n$-(Ar)-(CH$_2$)$_m$ represents 4-chlorophenyl, $R_2$ is other than ethyl.

DETAILED DESCRIPTION OF THE INVENTION

In Formulas I, II and III, halogeno preferably represents chloro or fluoro, and methyl and ethyl are the preferred lower alkyl moieties, although all the straight and branched manifestations thereof are included. Lower alkoxy radicals include ethers having alkyl moieties paralleling the $C_{1-6}$ alkyl group. When "Ar" is phenyl, n is preferably one, representing a mono-substituted phenyl moiety with the R-substituent being a group located at any of the ortho, meta or para positions. When n is 2, the 2,3-, 2,4-, 2,5-, 2,6-, 3,4-, or 3,5-positions are contemplated. Preferably $R_1$ and $R_2$ each represents methyl or ethyl.

Representative moieties when "Ar" represents a heterocycle are 2-, 3- or 4-pyridyl, 2- or 3-thienyl, pyrrol-2-yl, and N-alkylpyrrol-3-yl. Preferred is 2-thienyl, with or without an R substituent. State of the art salts of these triazoles may be employed, with the hydrochloride being one of convenience and general applicability. These salts are formed by standard techniques well known in the art.

When "Ar" represents naphthyl the preferred isomer is 2-naphthyl, with the R moiety being attached thereto at any of the available positions, although positions 5-, 6-, 7- or 8- are preferred for either the mono- or disubstituted naphthyl compounds of Formula I.

The thioethers of Formula I may be prepared using processes and procedures analogously known in the art as depicted in Scheme A.

Reaction Scheme A:

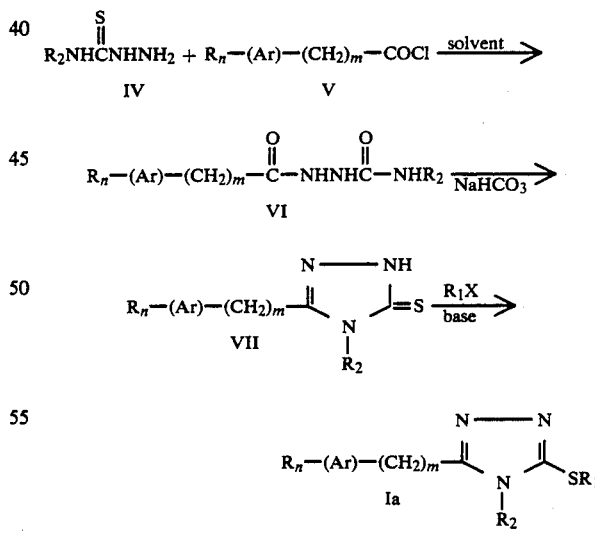

wherein $R_1$, $R_2$ and $R_n$-(Ar)-(CH$_2$)$_m$ are as defined for Formula I, and X is a suitable leaving group.

The sulfoxides and sulfones of Formula I may be prepared by oxidizing the alkylthioethers of Formula Ia with a peracid, preferably m-chloroperoxybenzoic acid (MCPBA), as seen in the following Scheme B.

Reaction Scheme B:

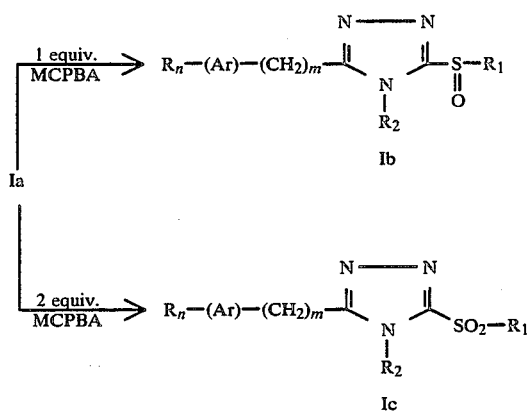

wherein $R_1$, $R_2$ and $R_n$-(Ar)-(CH$_2$)$_m$ are as defined for Formula I.

The preparation of the $R_2$-substituted thiosemicarbazides (IV) is readily effected by reacting a hydrazine with an isothiocyanate in a suitable solvent. The reaction is quite rapid and may be carried out between 0° C. and room temperature. Although the reaction proceeds rapidly, the mixture may be left for up to 24 hours without significant decrease in yield Reflux conditions may be employed but are not preferred. Almost all solvents may be used. Anhydrous alcohols (preferably ethanol or methanol) are preferred, although dimethylformamide (DMF), CHCl$_3$, CH$_2$Cl$_2$, tetrahydrofuran (THF) and Et$_2$O may also be used. The required hydrazines and isothiocyanates are readily available but may be prepared by known techniques quite obvious to one of ordinary skill in the art. Once obtained, the thiosemicarbazides are converted to their corresponding aroyl-substituted thiosemicarbazides (VI) by reaction with an appropriate acid chloride (V) in an aprotic solvent such as pyridine, CHCl$_3$, THF, and the like. The acylation proceeds rather easily at temperatures ranging from 0° C. to room temperature over periods of 3 to 24 hours, although elevated temperatures (e.g., reflux temperatures) may be employed. Again, the acid halides (V) generally are commercially available but may also be prepared from the corresponding acids which are available from obvious starting materials.

The aroyl thiosemicarbazides (VI) are subjected to a cyclization reaction which yields 3-aryl-3H-1,2,4-triazole-5-thiones of formula VII. The cyclization reaction is effected by heating the compounds (VI) in an aqueous base such as sodium bicarbonate or sodium hydroxide. Alcoholic bases may be utilized but generally are less desirable. The reaction is conducted at about the reflux temperature of the solvent, preferably at about 65°-100° C.

The preparation of the alkylthioethers (Ia) is readily effected by standard alkylation procedures. Preferably the 3-aryl-3H-1,2,4-triazole-5-thiones (VII) are reacted with the appropriate alkyl halide (R$_1$X) or a functional equivalent thereof in the presence of a mild base. Suitable bases are alkali metal carbonates or bicarbonates or alkali metal hydroxides, with K$_2$CO$_3$ or aqueous NaOH being preferred. It is preferred to use an alkyl iodide for the alkylation reaction, but any suitable leaving group (e.g., bromide or —OSO$_2$CF$_3$) may be used instead of the iodide. Suitable solvents are acetone, aqueous ethanol, THF, pyridine, and the like. The reaction may be carried out at temperatures ranging from room temperature to the reflux temperature of the reaction mixture, and in general the reaction takes about 15 hours or longer.

The conversion of the 3-aryl-4-alkyl-5-alkylthio-4H-1,2,4-triazoles (Ia) to their higher oxidation state is preferably effected by oxidizing the alkylthioethers (Ia) with a peracid according to well known conditions. Suitable oxidizing agents are H$_2$O$_2$ and NaIO$_4$, but m-chloroperoxybenzoic acid is preferred. In effecting the oxidation to the sulfinyl derivatives of Formula Ib, 1 molar equivalent of the peracid is used while 2 equivalents of the peracid will yield the sulfonyl derivatives of Formula Ic. The oxidations are carried out at temperatures of about 0° C. to room temperature in solvents which themselves are not susceptible to oxidation. Preferred solvents are CH$_2$Cl$_2$, CHCl$_3$, acetic acid and ethyl acetate.

Thioethers of Formula Ia have previously been found to be useful as pesticides, bactericides and fungicides, but have not previously been shown to possess muscle relaxant, spasmolytic, anticonvulsant or anxiolytic activity. 3-(4-Chlorophenyl)-4-methyl-5-methylsulfonyl-4H-1,2,4-triazole was found by M. Y. Mhasalkar, et al. (J. Med. Chem. 14(3), 260-2 (1971)), to have hypoglycemic activity, but neither that compound nor other sulfones of Formula Ic have previously been reported to have muscle relaxant, spasmolytic, anticonvulsant or anxiolytic activity.

It has now been discovered that previously known thioethers and sulfones of Formula I, as well as the novel sulfoxides and sulfones of Formulas II and III, exhibit pharmacological effects generally attributed to muscle relaxants, spasmolytics, anti-convulsants and anxiolytics, and thus the compounds of this invention will provide relief in patients suffering from muscle tension, muscle spasms and the pain associated therewith, convulsant seizures and anxiety.

Compounds that antagonize the tonic extensor seizures caused by strychnine have been shown to have muscle relaxant, spasmolytic, anticonvulsant and anxiolytic activities in man. The activity of the compounds can be demonstrated by the method of R. A. Turner, Screening Methods in Pharmacology, Chapter 14 (Academic Press, 1965). Groups of 10 to 20 male mice are administered one or more doses of test compound in an appropriate vehicle or, for comparison, the vehicle alone. At a selected time thereafter, strychnine sulfate, prepared as a solution in distilled water, is administered intraperitoneally at a dose of 2.7 mg/kg Ninety-nine percent of vehicle-treated mice exhibit convulsions at this dose of strychnine. Absence of tonic extension for greater than 15 minutes after strychnine administration is considered significant protection.

Treatment of mice with a dosage range of baclofen, a known anti-spastic/muscle relaxant, of from 12.5 to 200 mg/kg i.p. causes over 50% antagonism of strychnine-induced seizures, but no dose causes 100% protection. Tizanidine, a known muscle relaxant, causes maximal protection of 60% at 3.1 mg/kg i.p., but doses of up to 50 mg/kg do not cause a greater effect. Diazepam, a known anxiolytic with muscle relaxant and anticonvulsant activity, causes a dose-related inhibition with an ED$_{50}$ of 1.2 mg/kg i.p.; however very high doses are required for total inhibition of strychnine-induced seizures In contrast, many of the compounds of the present invention protect 100% against strychnine seizures at doses in the range of 4 times the $ED_{50}$. Among the compounds of this invention, the intraperitoneally administered $ED_{50}$ is 8.1 mg/kg for 4-methyl-3-phenyl-5-ethylsulfinyl-4H-1,2,4-triazole; 8.5 mg/kg for 4-methyl-3-phenyl-5-ethylsulfonyl-4H-1,2,4-triazole; 12.8 mg/kg for 4-methyl-3-phenyl-5-methylsulfonyl-4H-1,2,4-triazole; and 18.6 mg/kg for 4-methyl-3-(2-fluorophenyl)-5-ethylthio-4H-1,2,4-triazole.

In their use, the compounds of this invention will exert a relatively quick onset of action and have a prolonged duration of activity. The preferred use is in the treatment of muscle spasms and muscle tension. In general, the compounds will exert their therapeutic effects at dose levels of about 0.25–25 mg/kg of body weight per day although, of course, the degree of severity of the disease state, the age of the patient and other factors determined by the attending diagnostician will influence the exact course and dosage regimen suitable for each patient. In general the parenterally administered dose of the active compounds is about equivalent to that of the orally administered dose.

For oral administration, the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose or cornstarch. In another embodiment, the compounds of general formula I can be tableted with conventional tablet bases such as lactose, sucrose and cornstarch in combination with binders such as acacia, cornstarch or gelatin, disintegrating agents such as potato starch or alginic acid, and a lubricant such as stearic acid or magnesium stearate.

For parenteral administration, the compounds may be administered as injectable dosages of a solution or suspension of the compound in a physiologically acceptable diluent with a pharmaceutical carrier which can be a sterile liquid such as water, alcohols, oils and other acceptable organic solvents, with or without the addition of a surfactant and other pharmaceutically acceptable adjuvants. Illustrative of oils which can be employed in these preparations are those of petroleum, animal, vegetable, or synthesic origin, for example, peanut oil, soybean oil and mineral oil. In general, water, saline, aqueous dextrose and related sugar solutions, ethanol, glycols such as propylene glycol or polyethylene glycol, or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert material such as biodegradable polymers or synthetic silicones, for example Silastic ®, a silicone rubber manufactured by the Dow-Corning Corporation.

As is true in many classes of compounds with a pharmacological activity having a therapeutic end-use application, certain subgeneric groups and certain specific members of the class, because of their overall therapeutic index and their biochemical and pharmacological profile, are preferred. In this instance the preferred compounds of formula I are those wherein $R_1$ and $R_2$ groups are methyl or ethyl, those wherein the R substituent is chloro or fluoro, those wherein the Rn substituent is a monochloro or a monofluoro substituent, those wherein n is zero, those wherein m is zero, and those compounds wherein Ar is phenyl. Specifically preferred compounds are:

4-methyl-3-phenyl-5-methylsulfonyl-4H-1,2,4-triazole,
5-ethylsulfinyl-4-methyl-3-phenyl-4H-1,2,4-triazole,
5-ethylsulfonyl-4-methyl-3-phenyl-4H-1,2,4-triazole,
4-methyl-5-methylsulfinyl-3-phenyl-4H-1,2,4-triazole,
5-ethylthio-3-(2-fluorophenyl)-4-methyl-4H-1,2,4-triazole,
3-(2-fluorophenyl)-4-methyl-5-methylsulfonyl-4H-1,2,4-triazole,
3-(2-fluorophenyl)-4-methyl-5-methylthio-4H-1,2,4triazole,
3-(2-fluorophenyl)-4-methyl-5-methylsulfinyl-4H-1,2,4-triazole,
3-(4-fluorophenyl)-4-methyl-5-methylthio-4H-1,2,4triazole,
3-(2-chlorophenyl)-4-methyl-5-methylthio-4H-1,2,4triazole,
4-ethyl-3-(2-fluorophenyl)-5-methylthio-4H-1,2,4-triazole, and
5-ethylthio-4-methyl-3-phenyl-4H-1,2,4-triazole.

The following specific examples are given to illustrate the preparation of the compounds of this invention, although the scope of compounds exemplified is not meant to be limiting, this being so in view of the ease by which the compounds of formula I may be prepared Interchange, or modification, and employment of the necessary intermediates and solvents are quite obvious to a chemist of ordinary skill.

EXAMPLE 1

1-(2-Fluorobenzoyl)-4-methylthiosemicarbazide

To a stirred room temperature suspension of 4-methylthiosemicarbazide (7.9 g, $7.5 \times 10^{-2}$ mole) and $CHCl_3$ (190 ml), 2-fluorobenzoyl chloride (9.4 ml $7.9 \times 10^{-2}$ mole) was added dropwise. After stirring overnight at room temperature, the precipitate was collected by filtration and the product was washed with two portions of $Et_2O$. Drying by suction gave a colorless powder 11.3 g (66%) which was used without further purification in the subsequent cyclization step.

Alternate procedure:

To a stirred room temperature solution of 4-methylthiosemicarbazide (10.5 g, $1.00 \times 10^{-1}$ mole) and pyridine (250 ml), 2-fluorobenzoyl chloride (11.9 ml, $1.00 \times 10^{-1}$ mole) was added dropwise. After stirring overnight at room temperature the excess pyridine was evaporated at reduced pressure first on a rotary evaporator and then at high vacuum. This afforded a mixture of the desired product and pyridine hydrochloride which is used without further purification in the subsequent cyclization step.

EXAMPLE 2

1-(4-Pyridoyl)-4-methylthiosemicarbazide

4-Pyridoyl chloride hydrochloride (10.0 g, $5.62 \times 10^{-2}$ mole) and 4-methylthiosemicarbazide (5.91 g, $5.62 \times 10^{-1}$ mole) were stirred at room temperature in pyridine (150 ml). After stirring overnight, the pyridine was evaporated at reduced pressure and the concentrate was washed with $H_2O$. The undissolved product was collected by filtration and dried by suction.

EXAMPLE 3

1-(2-Thenoyl)-4-methylthiosemicarbazide

A stirred mixture of 2-thiophene carboxylic acid hydrazide (4.75 g, $3.34 \times 10^{-2}$ mole) and THF (115 ml) was warmed with a heat gun until homogeneous. A solution of freshly distilled methyl isothiocyanate (2.56 g, $3.51 \times 10^{-2}$ mole) and THF (5 ml) was then added dropwise. After being stirred for about 14 hours the precipitate was collected by filtration, washed with a little Et$_2$O, and dried by suction affording a colorless powder: 7.1 g (99%).

EXAMPLE 4

4-Methyl-1-(2-naphhthoyl)thiosemicarbazide

To a stirred room temperature solution of 4-methylthiosemicarbazide (5.91 g, $5.62 \times 10^{-2}$ mole) and pyridine (150 ml) was added 2-naphthoyl chloride (10.7 g, $5.61 \times 10^{-2}$ mole). After stirring overnight, the pyridine was evaporated at reduced pressure. The concentrate was treated with water and the undissolved product was collected by filtration and dried by suction

EXAMPLE 5

5-(2-Fluorophenyl)-2,4-dihydro-4-methyl-3H-1,2,4-triazole-3-thione 1-(2-Fluorobenzoyl)-4-methylthiosemicarbazide (11.3 g, $4.97 \times 10^{-2}$ mole) or the aforementioned mixture of the above and pyridine hydrochloride and 1 molar aqueous NaHCO$_3$ (480 ml, $4.80 \times 10^{-1}$ mole) were stirred and heated to reflux After refluxing overnight, the reaction was cooled in an ice bath before being acidified by the drop-wise addition of concentrated hydrochloric acid (40 ml, $4.8 \times 10^{-1}$ mole). The resulting precipitate was collected by filtration, washed with a little H$_2$O, and dried by suction. This afforded a colorless powder 5.0 g (48%). This material was of sufficient purity to go on to the next step. If desired this material could be crystallized from EtOAc/hexane affording colorless needles, mp 137°-139° C.

EXAMPLE 6

2,4-Dihydro-4-methyl-5-(4-pyridyl)-3H-1,2 4-triazole-3-thione 1-(4-Pyridoyl)-4-methylthiosemicarbazide (10.4 g, $4.97 \times 10^{-2}$ mole) and 1 molar aqueous NaHCO$_3$ (480 ml $4.80 \times 10^{-1}$ mole) were stirred and heated to reflux. After refluxing overnight, the reaction was cooled in an ice bath before being acidified by the dropwise addition of concentrated hydrochloric acid (40 ml, $4.8 \times 10^{-1}$ mole). The product was collected by filtration and dried by suction.

EXAMPLE 7

2,4-Dihydro-4-methyl-5-(2-thienyl)-3H-1,2,4-triazole-3-thione 1-(2-Thenoyl)-4-methylthiosemicarbazide (7.1 g, $3.3 \times 10^{-1}$ mole) and 1 molar aqueous NaHCO$_3$ (330 ml, $3.30 \times 10^{-1}$ mole) were stirred and heated to reflux. After refluxing about 14 hours the reaction was filtered while hot and the filtrate was then cooled in an ice bath. Acidification by the dropwise addition of concentrated HCl (28 ml, $3.4 \times 10^{-1}$ mole) gave a colorless precipitate which was collected by filtration, washed with a little cold H$_2$O, and dried by suction. Crystallization from isopropanol gave colorless spears: 5.0 g (77%), mp 155°-157° C.

EXAMPLE 8

2,4-Dihydro-4-methyl-5-(2-naphthyl)-3H-1,2,4-triazol-3-thione

4-Methyl-1-(2-naphthoyl)thiosemicarbazide (12.9 g, $4.97 \times 10^{-2}$ mole) and 1 molar aqueous NaHCO$_3$ (480 ml, $4.80 \times 10^{-1}$ mole) were stirred and warmed to reflux After refluxing overnight, the reaction was cooled in an ice bath before being acidified by the dropwise addition of concentrated hydrochloric acid (40 ml, $4.8 \times 10^{-1}$ mole). The resulting product was collected by filtration and dried by suction. Mp 223°-225° C.

EXAMPLE 9

3-(2-Fluorophenyl)-4-methyl-5-methylthio-4H-1,2,4-triazole

A mixture of 5-(2-fluorophenyl)-2 4-dihydro-4-methyl-3H-1,2,4-triazole-3-thione (4.56 g $2.18 \times 10^{-2}$ mole), K$_2$CO$_3$ (3.01 g, $2.18 \times 10^{-2}$ mole), methyl iodide (1 5 ml $2.4 \times 10^{-2}$ mole), and acetone (65 ml) was stirred and warmed to reflux. After refluxing overnight, the solvent was evaporated and the concentrate was treated with water. The aqueous mixture was extracted three times with EtOAc. The EtOAc extracts were combined washed with saturated aqueous NaCl, and dried over anhydrous Na$_2$SO$_4$. The drying agent was removed by filtration and the filtrate was evaporated at reduced pressure affording a pale yellow oil which was purified by chromatography and kugel rohr distillation, affording a pale yellow oil 3.55 g (73%), bp = 190°-197° C. (0.3 mm).

EXAMPLE 10

4-Methyl-5-methylthio-3-(4-pyridyl)-4H-1,2,4-triazole

A mixture of 2,4-dihydro-4-methy-5-(4-pyridyl)-3H-1,2,4-triazole-3-thione (4.19 g, $2.18 \times 10^{-2}$ mole), K$_2$CO$_3$ (3.01 g, $2.18 \times 10^{-2}$ mole), methyl iodide (1.5 ml, $2.4 \times 10^{-2}$ mole), and acetone (65 ml) was stirred and warmed to reflux. After refluxing overnight, the solvent was evaporated at reduced pressure and the concentrate was treated with water. The aqueous mixture was extracted with EtOAc three times. The EtOAc extracts were combined, washed with saturated aqueous NaCl, and dried over anhydrous Na$_2$SO$_4$. The drying agent was removed by filtration and the filtrate was evaporated at reduced pressure to yield the desired product.

EXAMPLE 11

3-(2-Thienyl)-4-methyl-5-methylthio-4H-1 2 4-triazole

A solution of methyl iodide (6.3 ml, $1.0 \times 10^{-1}$ mole) in ethanol (32 ml) was added dropwise to a stirred, room temperature solution of 2,4-dihydro-4-methyl-5-(2-thienyl)-3H-1,2,4-triazole-3-thione (12.5 g, $6.34 \times 10^{-2}$ mole) and 1 molar aqueous NaOH (142 ml, $1.42 \times 10^{-1}$ mole). After being stirred for about 14 hours the reaction was extracted four times with EtOAc. The EtOAc extracts were combined, washed with saturated aqueous NaCl, and dried over anhydrous Na$_2$SO$_4$. The drying agent was removed by filtration and the filtrate was evaporated at reduced pressure giving a tacky yellow solid which was purified by flash chromatography (EtOAc). Crystallization from EtOAc gave colorless crystals: 10.5 g (78%), mp 83°-85° C.

EXAMPLE 12

4-Methyl-5-methylthio-3-(2-naphthyl)-4H-1,2,4-triazole

A mixture of 2,4-dihydro-4-methyl-5-(2-naphthyl)-3-H-1,2,4-triazole-3-thione (5.26 g, $2.18 \times 10^{-2}$ mole), $K_2CO_3$ (3.01 g, $2.18 \times 10^{-2}$ mole), methyl iodide (1.5 ml, $2.4 \times 10^{-2}$ mole), and acetone (65 ml) was stirred and warmed to reflux. After refluxing overnight, the solvent was evaporated at reduced pressure and the concentrate was treated with water. The aqueous mixture was extracted with EtOAc three times. The EtOAc extracts were combined, washed with saturated aqueous NaCl, and dried over anhydrous $Na_2SO_4$. The drying agent was removed by filtration and the filtrate was evaporated at reduced pressure to yield the desired product Mp 177°–179° C.

EXAMPLE 13

3-(2-Fluorophenyl)-4-methyl-5-methylsulfinyl-4H-1,2,4-triazole

To a stirred, 0° C., solution of 3-(2-fluorophenyl)-4-methyl-5-methylthio-4H-1,2,4-triazole (5.0 g, $2.2 \times 10^{-2}$ mole) and $CH_2Cl_2$ (125 ml) was added portionwise m-chloro-peroxybenzoic acid (4.83 g, $2.24 \times 10^{-2}$ mole, 80% active MCPBA). After stirring overnight at room temperature, the reaction was diluted with $CH_2Cl_2$ until homogeneous then washed in turn twice with saturated aqueous $NaHCO_3$ and once with saturated aqueous NaCl. After drying over anhydrous $Na_2SO_4$, the $CH_2Cl_2$ was evaporated leaving an oil which slowly crystallized. Crystallization from EtOAc/hexane gave a colorless solid 3.7 g (68%), mp 95°–97° C.

EXAMPLE 14

4-Methyl-5-methylsulfinyl-3-(4-pyridyl)-4H-1,2,4-triazole

To a stirred, 0° C., solution of 4-methyl-5-methylthio-3-94-pyridyl)-4H-1,2,4-triazole (4.54 g, $2.2 \times 10^{-2}$ mole) and $CH_2Cl_2$ (125 ml) was added portionwise m-chloroperoxybenzoic acid (4.83 g, $2.24 \times 10^{-2}$ mole, 80% active MCPBA). After stirring overnight the reaction was diluted with $CH_2Cl_2$ until homogeneous. The $CH_2Cl_2$ solution was then washed with saturated aqueous $NaHCO_3$ and saturated aqueous NaCl. After drying over anhydrous $Na_2SO_4$, the $CH_2Cl_2$ was evaporated at reduced pressure to give the desired product.

EXAMPLE 15

3-(2-Thienyl)-4-methyl-5-methylsulfinyl-4H-1,2,4-triazole

To a stirred, 0° C., solution of 4-methyl-5-methylthio-3-(2-thienyl)-4H-1,2,4-triazole (4.85 g, $2.29 \times 10^{-2}$ mole) and $CH_2Cl_2$ (170 ml) was added portionwise m-chloroperoxybenzoic acid (4.95 g, $2.29 \times 10^{-2}$ mole). After stirring at room temperature overnight the reaction was washed two times with saturated aqueous $NaHCO_3$ and one time with saturated aqueous NaCl, and dried over anhydrous $N_2SO_4$. The drying agent was removed by filtration and the filtrate was evaporated at reduced pressure yielding an off-white solid which was purified by flash chromatography (40% acetone/EtOAc). Crystallization from EtOAc afforded small colorless plates: 2.78 g (53%), mp 10520–107° C.

EXAMPLE 16

4-Methyl-5-methylsulfinyl-3-(2-naphthyl)-4H-1,2,4-triazole

To a stirred, 0° C., solution of 4-methyl-5-methylthio3-(2-naphthyl)-4H-1,2,4-triazole (4.00 g, $1.57 \times 10^{-2}$ mole) and $CH_2Cl_2$ (110 ml) was added portionwise m-chloroperoxybenzoic acid (3.38 g, $1.57 \times 10^{-2}$ mole). After stirring overnight at room temperature the reaction was diluted with $CH_2Cl_2$ (200 ml), washed two times with saturated aqueous $NaHCO_3$ and one time with saturated aqueous NaCl, and dried over anhydrous $N_2SO_4$. The drying agent was removed by filtration and the filtrate was evaporated at reduced pressure leaving an off-white solid which was purified by flash chromatography (4% $CH_3OH/CH_2Cl_2$). Crystallization from toluene afforded small colorless plates: 2.5 g (59%), mp 224°–226° C.

EXAMPLE 17

3-(2-Fluorophenyl)-4-methyl-5-methylsulfinyl-4H-1,2,4-triazole

To a stirred, 0° C., solution of 3-(2-fluorophenyl)-4-methyl-5-methylthio-4H-1,2,4-triazole (5.0 g, $2.2 \times 10^{-2}$ mole) and $CH_2Cl_2$ (125 ml) was added portionwise m-chloroperoxybenzoic acid (12.1 g, $5.6 \times 10^{-2}$ mole, 80% active MCPBA). After stirring overnight at room temperature, the reaction was diluted with $CH_2Cl_2$ until homogeneous and was then washed in turn twice with saturated aqueous $NaHCO_3$ and once with saturated aqueous NaCl. After drying over anhydrous $Na_2SO_4$, the $CH_2Cl_2$ was evaporated at reduced pressure leaving a solid which was purified by chromatography and subsequent crystallization from EtOAc/hexane giving colorless matted needles: 3.6 (63%), mp 128°–130° C.

EXAMPLE 18

4-Methyl-5-methylsulfonyl-3-(4-pyridyl)-4H-1,2,4-triazole

To a stirred, 0° C., solution of 4-methyl-5-methylthio-3-(4-pyridyl)-4H-1,2,4-triazole (4.54 g, $2.2 \times 10^{-2}$ mole) and $CH_2Cl_2$ (125 ml) was added portionwise m-chloroperoxybenzoic acid (9.49 g, $4.4 \times 10^{-2}$ mole, 80% active MCPBA). The reaction was stirred for 1 hour at 0° C. then allowed to warm to room temperature. After stirring overnight, the reaction was diluted with $CH_2Cl_2$ until homogeneous. The $CH_2Cl_2$ solution was then washed in turn with saturated aqueous $NaHCO_3$ and saturated aqueous NaCl. After drying over anhydrous $Na_2SO_4$, the $CH_2Cl_2$ was evaporated at reduced pressure to yield the desired product.

EXAMPLE 19

3-(2-Thienyl)-4-methyl-5-methylsulfonyl-4H-1,2,4-triazole

To a stirred, 0° C., solution of 4-methyl-5-methylthio-3-(2-thienyl)-4H-1,2,4-triazole (3.00 g, $1.42 \times 10^{-2}$ mole) and $CH_2Cl_2$ (105 ml) was added portionwise m-chloroperoxybenzoic acid (6.42 g, $2.98 \times 10^{-2}$ z mole). After stirring overnight at room temperature, the reaction was washed two times with saturated aqueous $NaHCO_3$ and one time with saturated NaCl, and dried over anhydrous $N_2SO_4$. The drying agent was removed by filtration and the filtrate was evaporated at reduced pressure, leaving an off-white solid which was purified by flash chromatography (20% EtOAc/CH2Cl2). Crystallization from EtOAc/hexane afforded a colorless solid 3.5 g (76%), mp 157°–159° C.

EXAMPLE 20

4-Methyl-5-methylsulfonyl-3-(2-naphthyl)-4H-1,2,4-triazole

To a stirred, 0° C., solution of 4-methyl-5-methylthio-3-(2-naphthyl)-4H-1,2,4-triazole (5.62 g, 2.20×10$^{-2}$ mole) and CH2Cl2 (125 ml) was added portionwise m-chloroperoxybenzoic acid (12.1 g, 5.6×10$^{-2}$ mole, 80% active MCPBA). The reaction was stirred at 0° C for 1 hour and then allowed to warm to room temperature After stirring overnight, the reaction was diluted with CH2Cl2 until homogeneous. The CH2Cl2 solution was then washed in turn with saturated aqueous NaHCO3 and saturated aqueous NaCl. After drying over anhydrous Na2SO4, the CH2Cl2 was evaporated at reduced pressure to afford the desired product, which was recrystallized. Mp 204°–6° C.

By substituting the appropriate acid chlorides in the procedure of Example 1 and reacting the resulting thiosemicarbazide according to the procedures of Examples 5, 9, 13 and 17, the tabulated compounds of Formula I are obtained.

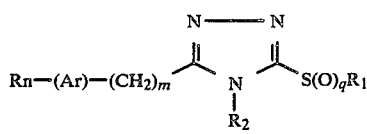

| Rn—(Ar)—(CH2)m | q | R1 | R2 | mp (°C.) |
|---|---|---|---|---|
| phenyl | 0 | CH3 | CH3 | 134–136 |
| phenyl | 1 | CH3 | CH3 | 144–146 |
| phenyl | 2 | CH3 | CH3 | 158–160 |
| phenyl | 0 | C2H5 | CH3 | 94–99 |
| phenyl | 1 | C2H5 | CH3 | 131–133 |
| phenyl | 2 | C2H5 | CH3 | 141–143 |
| 4-fluorophenyl | 0 | CH3 | H | 145–146 |
| 4-fluorophenyl | 0 | CH3 | CH3 | 193–195 |
| 2-fluorophenyl | 0 | CH3 | C2H5 | oil |
| 2-fluorophenyl | 0 | C2H5 | CH3 | 95–97 |
| 2-fluorophenyl | 1 | C2H5 | CH3 | 63–67 |
| 2-fluorophenyl | 2 | C2H5 | CH3 | 145–147 |
| 2-chlorophenyl | 0 | CH3 | CH3 | oil |
| 4-chlorophenyl | 0 | CH3 | CH3 | 105–107 |
| 4-chlorophenyl | 0 | CH3 | C2H5 | 113–115 |
| 4-methoxyphenyl | 0 | CH3 | CH3 | 149–151 |
| 4-methoxyphenyl | 1 | CH3 | CH3 | 168–170 |
| 4-methoxyphenyl | 2 | CH3 | CH3 | 187–189 |
| 4-tolyl | 0 | CH3 | CH3 | 140–142 |
| 4-tolyl | 1 | CH3 | CH3 | 161–163 |
| 4-tolyl | 2 | CH3 | CH3 | 170–172 |

We claim:

1. A method for the treatment of anxiety to a patient in need thereof which comprises administering a therapeutically effective amount of a compound of the formula

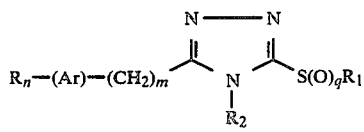

or a pharmaceutically acceptable salt thereof wherein
Ar is phenyl or naphthyl;
R1 is C1-6 lower alkyl;
R2 is hydrogen or C1-6 lower alkyl;
R is C1-6 lower alkyl, C1-6 alkoxy, hydroxy, halogeno, or trifluoromethyl and n is zero, 1 or 2, or Rn-(Ar) is methylenedioxyphenyl; and each of m and q is zero, 1 or 2.

2. A method of claim 1 wherein Ar is phenyl.
3. A method of claim 2 wherein m is zero.
4. A method of claim 1 wherein n is zero or one, m is zero, R is halogeno, and R1 and R2 are independently methyl or ethyl.
5. A method of claim 4 wherein q is zero.
6. A method of claim 4 wherein q is one.
7. A method of claim 4 wherein q is two.
8. A method of claim 1 wherein said compound is selected from the group consisting of
4-methyl-3-phenyl-5-methylsulfonyl-4H-1,2,4-triazole,
4-methyl-3-phenyl-5-ethylsulfonyl-4H-1,2,4-triazole,
5-ethylthio-3-(2-fluorophenyl)-4-methyl-4H-1,2,4-triazole,
3-(2-fluorophenyl)-4-methyl-5-methylsulfonyl-4H-1,2,4-triazole, and
4-methyl-3-phenyl-5-ethylsulfinyl-4H-1,2,4-triazole.

* * * * *

UNITED STATES PATENT AND TRADEMARK OFFICE
CERTIFICATE OF

PATENT NO. : 4,981,863
DATED : 1/1/91
INVENTOR(S) : Kane et al.

It is certified that error appears in the above-identified patent and that said Letters Patent is hereby corrected as shown below:

Column 2, Line 45 patent reads:

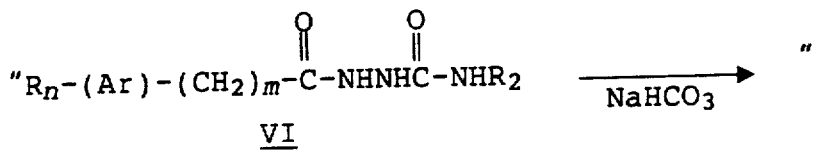

and should read:

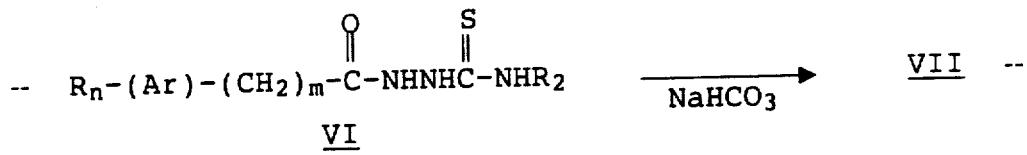

Column 4, line 23 patent reads "4-methyl" and should read --4-ethyl--.

Column 4, line 67 patent reads "seizures In contrast," and should read --seizures. In contrast,--.

Column 6, line 14 patent reads "1,2,4triazole," and should read -- 1,2,4-triazole, --.

Column 6, line 19 patent reads "1,2,4triazole," and should read -- 1,2,4-triazole, --.

Column 6, line 21 patent reads "1,2,4triazole," and should read -- 1,2,4-triazole, --.

UNITED STATES PATENT AND TRADEMARK OFFICE
CERTIFICATE OF

PATENT NO. : 4,981,863
DATED : 1/1/91
INVENTOR(S) : Kane et al.

It is certified that error appears in the above-identified patent and that said Letters Patent is hereby corrected as shown below:

Column 6, line 64 patent reads "$10^{-1}$" and should read -- $10^{-2}$ --.

Column 7, line 16 patent reads "(2-naphhthoyl)" and should read --(2-naphthoyl)--.

Column 7, line 33 patent reads "reflux After" and should read --reflux. After--.

Column 7, line 39 patent reads "powder 5.0" and should read --powder: 5.0--.

Column 7, line 45 patent reads "1,2 4-triazole" and should read -- 1,2,4-triazole --.

Column 7, line 61 patent reads "$10^{-1}$" and should read -- $10^{-2}$ --.

Column 8, line 5 patent reads "triazol" and should read --triazole--.

Column 8 line 20 patent reads "2 4-dihydro" and should read --2,4-dihydro--.

Column 8, line 22 patent reads "(1 5 ml 2.4" and should read --(1.5 ml, 2.4--.

Column 8, line 27 patent reads "combined washed" and should read --combined, washed--.

UNITED STATES PATENT AND TRADEMARK OFFICE
CERTIFICATE OF

PATENT NO. : 4,981,863
DATED : 1/1/91
INVENTOR(S) : Kane et al.

It is certified that error appears in the above-identified patent and that said Letters Patent is hereby corrected as shown below:

Column 8, line 39 patent reads "methy" and should read --methyl--.

Column 8, line 54 patent reads "1 2 4-triazole" and should read --1,2,4-triazole--.

Column 9, line 42 patent reads "3-94-pyridyl" and should read -- 3-(4-pyridyl) --.

Column 9, line 68 patent reads "10520-107° C" and should read --105-107° C--.

Column 10, line 5 patent reads "methylthio3" and should read --methylthio-3--.

Column 10, line 62 patent reads "$10^{-2}$ z mole)" and should read --$10^{-2}$ mole)--.

Column 11, line 17 patent reads "temperature After" and should read --temperature. After--.

Signed and Sealed this
Fifteenth Day of December, 1992

Attest:

DOUGLAS B. COMER

*Attesting Officer*      *Acting Commissioner of Patents and Trademarks*